United States Patent [19]
Pederson et al.

[11] Patent Number: 5,916,983
[45] Date of Patent: Jun. 29, 1999

[54] BIOLOGICALLY ACTIVE COMPOUNDS BY CATALYTIC OLEFIN METATHESIS

[75] Inventors: Richard L. Pederson, Bend, Oreg.; Robert H. Grubbs, South Pasadena, Calif.

[73] Assignee: Bend Research, Inc., Bend, Oreg.

[21] Appl. No.: 08/863,872

[22] Filed: May 27, 1997

[51] Int. Cl.$^6$ .................. C08F 4/72; C08F 4/80; C07F 14/00; C07C 29/12

[52] U.S. Cl. .............. 526/170; 526/171; 556/136; 568/886

[58] Field of Search ............... 568/886; 576/170, 576/171; 556/136

[56] References Cited

U.S. PATENT DOCUMENTS

| | | | |
|---|---|---|---|
| 3,825,607 | 7/1974 | Descolus et al. | 260/654 K |
| 4,189,614 | 2/1980 | Samain et al. | 568/908 |
| 4,609,498 | 9/1986 | Banasiak et al. | 568/1 |
| 4,654,461 | 3/1987 | Drake et al. | |
| 5,312,940 | 5/1994 | Grubbs et al. | |
| 5,342,909 | 8/1994 | Grubbs et al. | |

FOREIGN PATENT DOCUMENTS

WO96/04289  2/1996  WIPO.

OTHER PUBLICATIONS

Nguyen et al., "Ring–Opening Metathesis Polymerization (ROMP) of Norbornene by Group VIII Carbene Complex in Protic Media," 114 *J.A.C.S.* 3974 (1992).

Nguyen et al., "Syntheses and Activities of New Single–Component, Ruthenium–Based Olefin Metathesis Catalysts," 115 *J.A.C.S.* 9858 (1993).

Randall et al., "Selective Ring–Opening Cross–Metathesis. Short Syntheses of Multifidene and Viridiene," *J.A.C.S.* 9610 (1995).

Schwab et al., "Synthesis and Applications of $RuCl_2(=CHR')(PR_3)_2$: The Influence of the Alkylidene Moiety on Metathesis Activity," 118 *J.A.C.S.* 100 (1996).

Schneider et al., "Selective Ring–Opening Olefin Metathesis of Funtionalized Monosubstituted Olefins," 36 *Angew. Chem. Int. Ed. Engl.* 257 (1997).

*Primary Examiner*—John Kight
*Assistant Examiner*—Raymond Covington
*Attorney, Agent, or Firm*—Chernoff, Vilhauer McClung & Stenzel, LLP

[57] ABSTRACT

Biologically active compounds such as pheromones and precursors thereof are produced by catalyzed cross metathesis of dissimilar terminal olefins or of a cyclodiene and a terminal olefin.

13 Claims, No Drawings

BIOLOGICALLY ACTIVE COMPOUNDS BY CATALYTIC OLEFIN METATHESIS

BACKGROUND OF THE INVENTION

Pheromones are finding increasing acceptance as useful tools in pest control since they have been proven to be effective in disrupting the mating and reproductive cycles of specifically targeted insect species. In general, common pheromones are 10- to 18-carbon atom-containing olefins having a terminal alcohol, aldehyde or acetate functional group and possess a particular stereo-isomerism. A good example of a commercially viable pheromone is gossyplure, which is effective in controlling pink bollworm. Gossyplure comprises a mixture of 7,11-hexadecadienyl acetate stereoisomers, and a wide variety of synthesis routes to obtain this pheromone have been proposed. See, for example, U.S. Pat. Nos. 3,919,329, 3,996,270 and 4,296,042. A particularly simple synthesis route involves the disproportionation of 1,5-cyclooctadiene and 1-hexene in the presence of a disproportionation catalyst to yield the precursor 1,5,9-tetradecatriene (TDT) and other olefins, the TDT being subsequently converted to gossyplure. See, U.S. Pat. Nos. 4,609,498 and 4,654,461. However, to date this synthesis route has not been commercially attractive by virtue of its ability to produce but a single pheromone precursor and because of the low yields and selectivity obtained.

What is needed therefore is a simple method of synthesizing a wide variety of pheromone compounds and precursors that produces high yields and selectivity, and that is capable of producing stable and reproducible stereoisomeric ratios of products. These needs and others are met by the present invention which is summarized and described in detail herein.

SUMMARY OF THE INVENTION

The essence of the invention lies in the discovery that a particular catalyst is highly effective in promoting a metathesis coupling reaction between dissimilar olefins, at least one of which is a terminal olefin, to form a desirable class of stereospecific, internal generally conjugated olefinic compounds comprising pheromone precursors. More specifically, the catalyst is a nonconjugated alkylidene or benzylidene ruthenium phosphine complex of the structure

wherein L is a bulky substituted or unsubstituted linear or cyclic alkyl; A and A' are anions; and CRR' is a nonconjugated alkylidene. The class of dissimilar olefinic compounds contains from 10 to 18 carbon atoms in the hydrocarbon chains, one or two double bonds and a terminal functional group.

DETAILED DESCRIPTION OF PREFERRED EMBODIMENTS

The present invention comprises a method of synthesizing a biologically active compound of the structure I

      I comprising reacting two dissimilar olefins, at least one of which is a terminal olefin, selected from a cyclodiene containing from 7 to 12 carbon atoms and olefins of the structure II

      II in the presence of a catalyst of the structure $$[(PL_3)_2AA']Ru=CRR'$$

wherein a is selected from zero, 1 and 2;

b is selected from 1 and 2;

c is selected from zero and 1;

m and n are selected from zero and an integer so that the total number of carbon atoms in the hydrocarbon chain of structure I is from 10 to 18;

r and t are integers selected so that the combined total of carbon atoms in the hydro-carbon chains of the two dissimilar olefins of structure II is from 12 to 40;

z is an integer of from 1 to 10;

X, Y and Z are selected from hydrogen, halide methyl, acetyl, —CHO and —OR" wherein R" is selected from hydrogen and an alcohol protecting group selected from tetrahydropyranyl, tetrahydrofuranyl, t-butyl, trityl, ethoxyethyl and Si—$(R_1)(R_2)(R_3)$ wherein $R_1$, $R_2$ and $R_3$ are independently selected from alkyl and aryl;

L is selected from —$CR_4(R_5)_2$ and cycloalkyl or alkyl-substituted cycloalkyl wherein the number of carbon atoms in the ring is from 4 to 12;

$R_4$ and $R_5$ are each selected from hydrogen and alkyl;

A and A' are anionic ligands independently selected from halogen, hydrogen, $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonyl, $C_1$–$C_{20}$ alkylsulfonyl, $C_1$–$C_{20}$ alkylsulfinyl, each ligand optionally being substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy; and R and R' are independently selected from hydrogen, $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkysulfonyl and $C_1$–$C_{20}$ alkylsulfinyl, each of R and R' optionally substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy.

The method is capable of producing a variety of common useful pheromones either directly or indirectly, as in the case of the production of precursors of the pheromones. Exemplary pheromones and precursor pheromones producible by the invention method are gossyplure, peach twig borer pheromone, codling moth pheromone and leafroller pheromone.

THE CATALYST

The catalyst is one particular subset of a large class of Ru-based catalysts generically described by Grubbs et al. in PCT U.S. patent application Ser. No. 95/09,655 as being useful in olefin metathesis reactions. However, there is no recognition or suggestion therein of either this particular class of catalysts or of its utility in promoting the coupling reaction of the particular class of terminal olefins to obtain the biologically active products and precursors obtainable by the present invention.

In general, the catalyst may be prepared by adding alkyl- or aryl-substituted diazomethane to [(PPh$_3$)$_3$AA']Ru(II), followed by the addition of 2 equivalents of a trialkyl-substituted phosphine, then purified by recrystallization from dichloromethane and methanol, described in greater detail in Schwab et al., 118 JACS 100 (1996).

A preferred catalyst is one wherein the anions A and A' are independently selected from Cl$^-$, Br$^-$, CF$_3$COO$^-$, CH$_3$COO$^-$, CFH$_2$COO$^-$, CF$_2$HCOO$^-$, (CH$_3$)$_3$CO$^-$, (CF$_3$)$_2$CH$_3$CO$^-$, CF$_3$(CH$_3$)$_2$CO$^-$, PhO$^-$, CH$_3$O$^-$, CH$_3$CH$_2$O$^-$, CH$_3$PhSO$_3^-$, and CF$_3$SO$_3^-$. A particularly preferred catalyst is one wherein R and R' are independently selected from hydrogen, methyl and phenyl and wherein the anions A and A' are independently selected from Cl$^-$, Br$^-$ and CF$_3$COO$^-$; this is because chlorides and bromides are already present on the preferred catalyst precursors RuCl$_3$, Ru[Cl$_2$(PPh$_3$)$_3$] and the corresponding bromo-substituted compounds, and because the trifluoroacetate is readily prepared by reacting silver trifluoroacetate with the chloro- or bromo-substituted catalysts.

THE OLEFINIC REACTANTS

It has been discovered that the catalyst promotes a noticeably much faster reaction rate of terminal olefins as compared to internal olefins and so at least one of the two dissimilar olefins is preferably a terminal olefin. Similarly, contrary to what would be expected from the teachings of the prior art, when the catalyst is used in coupling olefins of the particular class disclosed herein, the desired class of product compounds is produced to the virtual exclusion of other metathesis homocouples or intermediates, with high yields and selectivity, and in highly desirable stereoisomeric ratios that remain constant throughout the reaction, the latter feature demonstrating that the reaction is essentially irreversible, also contrary to what would be expected from the prior art.

Exemplary olefinic reactants are 1,5-cyclooctadiene (COD) and 1-hexene to produce the gossyplure precursor TDT; 1-chloro-5-hexene and 1-hexene to produce the peach twig borer pheromone precursor 1-chloro-5-decene; 11-dodecenyl acetate and 1-butene to directly produce 11-tetradecenyl acetate (TDA), the leaf-roller pheromone; and an 8-nonenyl derivative having a terminal functional group with a 2,4-hexadiene or a 2-acetoxy-4-pentene to produce the Codling Moth pheromone trans, trans-8,10-dodecadienol or its precursor.

EXAMPLE 1

Synthesis of [(PCy$_3$)$_2$Cl$_2$]Ru=CHPh

A solution of RuCl$_2$(PPh$_3$)$_3$ (4.0 g 4.17 mmol) in CH$_2$Cl$_2$ (40 mL) was treated at −78° C. with a −50° C. solution of phenyldiazomethane (986 mg 8.35 mmol, 2.0 eq) in pentane (10 mL). Upon addition of the diazo compound, an instantaneous color change from orange-brown to green-brown and vigorous bubbling was observed. After the reaction mixture was stirred at −70 to −60° C. for 10 minutes an ice-cold solution of tricyclohexylphosphine (PCy$_3$) (2.57 g 9.18 mmol, 2.2 eq) in CH$_2$Cl$_2$ was added by syringe. The solution was allowed to warm to room temperature for 30 minutes while stirring, and exhibited a color change from brown-green to red. The solution was filtered, concentrated to half its original volume and filtered a second time. Methanol(1100 mL) was added to precipitate a purple microcrystalline solid, which was filtered, washed several times with acetone and methanol (10 mL portions) and dried under vacuum for several hours to yield 3.40 g [(PCy$_3$)$_2$Cl$_2$]Ru=CHPh (99%).

EXAMPLE 2

Peach Twig Borer (PTB) pheromone is a mixture of 5-decenyl acetate and 5-decenol of approximately 85:15 molar ratio of the acetate to the alcohol. The synthesis of PTB pheromoneqcouples 1-chloro-5-hexene and 1-hexene to yield 1-chloro-5-decene. 1-chloro-5-decene is converted to 5-decenyl acetate, isomerized and a portion of the acetate is hydrolyzed to the corresponding alcohol to yield PTB pheromone. The overall scheme using the catalyst of Example 1 is shown below, followed by details of the synthesis.

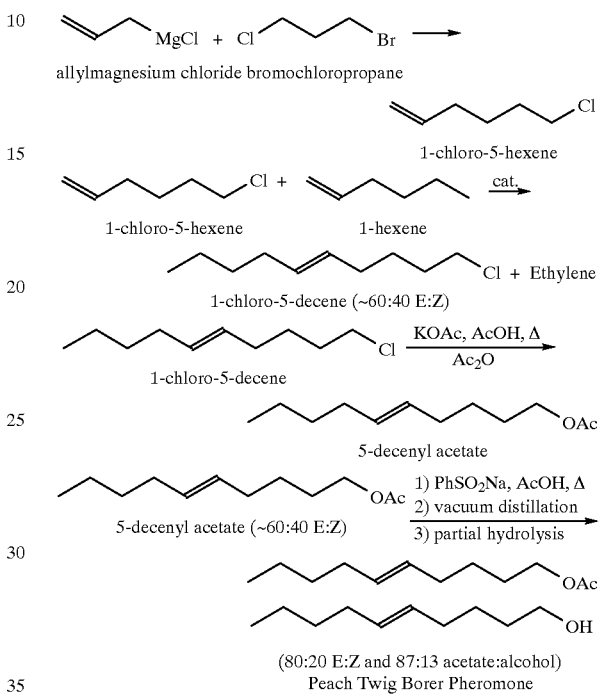

(80:20 E:Z and 87:13 acetate:alcohol)
Peach Twig Borer Pheromone

1-Chloro-5-decene was synthesized as follows: 200.1 g (1.61 mol 95% pure) of 1-chloro-5-hexene, 282 g (416 mL, 3.35 mol) of 1-hexene and 2.0 mL of α,α-dichlorotoluene (metal hydride inhibitor) were added to a dry 1-L 2-necked round-bottomed flask containing a reflux condenser and a stir bar. This mixture was sparged sub-surface with Argon. After 10 minutes 5.5 g (6.67 mol) of the metathesis catalyst of Example 1 was added. The mixture was placed in a 62° C. oil bath and stirred. Samples were taken periodically and analyzed by gas chromatography (GC) to determine the extent of conversion. After 3 hours, the reaction stopped and the catalyst was inactivated by the addition of 3 mL of ethyl vinyl ether. The catalyst was removed by filtering the mixture through 200 g of silica gel. The silica gel was rinsed with 500 mL of hexane and combined with the post-filtered reaction solution. 1-chloro-5-decene was purified by vacuum distillation to yield 105.9 g. This was converted to 5-decenyl acetate as follows.

105.9 g (0.61 mol) 1-Chloro-5-decene, 178.8 g (1.82 mol) potassium acetate, 188 g (1.84 mol) acetic anhydride and 109 g acetic acid were added to a dry 3-necked 1-L round-bottomed flask containing a reflux condenser and an overhead mechanical stirrer. This mixture was heated and stirred at 140° C. After 18 hours an additional 62 g of potassium acetate and 200 g acetic acid were added, and heating was continued for an additional 24 hours. The conversion to the corresponding acetate was 99% complete according to GC analysis. This acetylation reaction was quenched by pouring the still warm reaction mixture into a stirred ice/water slurry.

Upon quenching of the acetylation reaction, an organic and an aqueous phase formed and the aqueous phase was separated and washed with 500 mL of hexane, whereupon a second organic/aqueous phase separation occurred and the aqueous phase was removed. The two organic phases were combined and washed with sodium bicarbonate-saturated water, then dried with sodium sulfate, filtered and the hexane removed to yield 120 g of crude 5-decenyl acetate, which was purified by vacuum distillation ($Bpt_{1.0}$ 85–91° C.) to yield 76.7 g of >98% pure 5-decenyl acetate and 40 g of <98% pure of the same compound.

76.7 g of 5-Decenyl acetate (E:Z ratio of 61:39) and 0.41 g (6.67 mol %) of the sodium salt of benzene sulfinic acid and 6 mL of glacial acetic acid were added to a 250 mL round-bottomed flask. The solution was warmed to 80° C. for 18 hours under nitrogen. GC analysis indicated that the isomeric ratio had changed to 80:20 E:Z, representing theoretical thermodynamic equilibrium. The mixture was cooled to room temperature and vacuum distilled to yield 72.8 g of substantially pure 5-decenyl acetate.

A portion of the acetate is removed and converted to the corresponding alcohol as follows. 15.0 g (67 mmol) of the 5-decenyl acetate, 35 mL of methanol and 34 mL of 2 M sodium hydroxide were added to a 250 mL round-bottomed flask. This mixture was stirred for 3 hours at room temperature. After 3 hours the hydrolysis was complete, 10 mL of hexane was added and the solution was washed with 10 mL of 1 M HCl, 10 mL of $NaHCO_3$-saturated water and 10 mL of brine. The organic phase was dried with sodium sulfate, filtered and the hexane removed under reduced pressure to yield 9.4 g of 5-decenol. GC analysis showed the isometric ratio to be 80:20 E:Z.

Finally, PTB pheromone was prepared by blending 9.4 g (60.2 mmol) of the 80:20 E:Z 5-decenol and 79.5 g (402 mmol) of the 80:20 E:Z 5-decenyl acetate to make an 87:13 molar mixture of the acetate and alcohol.

EXAMPLE 3

The catalyst of Example 1 is used in a coupling reaction between 2,4-hexadiene and the 8-nonenyl derivative 8-nonen-1-yl chloride to produce the chloride precursor intermediate of the Codling Moth (CM) pheromone E,E-8,10-dodecadienol. The general reaction scheme is shown below, wherein X is halide or an alcohol with a protecting group; in this Example, X was Cl⁻.

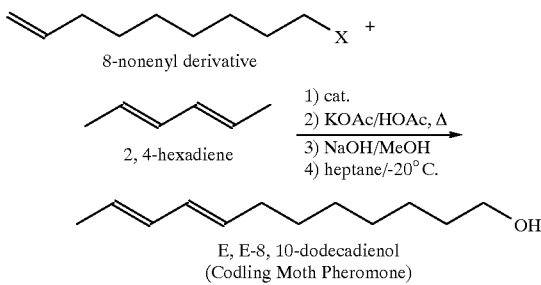

The nonenyl chloride was synthesized in a nitrogen-blanketed flask equipped with a reflux condenser and a magnetic stir bar. One mole (200 g) of bromochlor-ohexane and 100 mL of dry tetrahydrofuran (THF) were added, followed by addition of allylmagnesium chloride (500 mL of 2 M solution in THF) at a rate sufficient to cause gentle refluxing of the THF. This reaction was quenched by pouring its reactants into 250 mL of cool water. Two phases formed and the aqueous phase was removed. The organic phase was washed successively with 100 mL of 2 M sulfuric acid, 100 mL of sodium bicarbonate-saturated water, and 100 mL of brine. The organic phase was dried with anhydrous sodium sulfate, filtered and the THF removed under reduced pressure. The remaining light brown liquid is vacuum distilled ($Bpt_{2.0}$ 40–45° C.) to yield 176 g (850 mmol, 85% yield) of 8-nonen-1-yl chloride.

The so-produced nonenyl chloride (112 g; 700 mmol) was added to an equimolar amount of the 2,4-hexadiene in a 100 mL round-bottomed flask equipped with a magnetic stir bar and a reflux condenser, along with 6 g of α,α-dichlorotoluene. This solution was subsurface-sparged with nitrogen for 10 minutes. The catalyst of Example 1 (1.15 g; 1.4 mmol) was added and the reaction flask was placed in an 85° C. oil bath for 15 hours. The reaction was terminated by cooling to room temperature, followed by the addition of 300 ml of hexanes and filtering three times through 75 g of silica gel. Hexanes were removed under reduced pressure and the remaining liquid was vacuum distilled through a 2 cm×30 cm packed bed column to yield 12 g of 8-nonen-1-yl chloride ($Bpt_{1.5}$ 36–40° C.), 46.3 g of 8-decen-1-yl chloride ($Bpt_{1.5}$ 56–60° C.), 15.3 g of 8,10-dodecadien-1-yl chloride ($Bpt_{1.5}$ 90–91 C.), and 30.4 g of 76% purity 1,16-dichloro-8-hexadecene and high boilers that remained in the distillation pot.

The 8,10-dodecadien-1-yl chloride was converted to 8,10-dodecadien-1-yl acetate by heating with potassium acetate and acetic acid, followed by conversion of the acetate to CM pheromone by hydrolysis of the acetate with sodium hydroxide in methanol and recrystallization from heptane.

The particulars of the conversion of the dodecadienyl chloride to the alcohol that is CM pheromone are set forth below. To a 100 mL glass round-bottomed flask equipped with a reflux condenser, a stir bar and a nitrogen atmosphere were added 1.0 g (5 mmol) of 8,10-dodecadien-1-yl chloride, 8.1 g (8.3 mmol) potassium acetate and 40 ml of glacial acetic acid. This mixture was placed in a 150° C. oil bath for 76 hours, after which time GC analysis indicated that the reaction was >98% complete. The reaction mixture was poured into 100 ml of water and ice and stirred for one hour. Ethyl acetate (100 ml) was added and the organic phase was separated from the aqueous phase. The organic phase was washed with 4×50 mL of sodium bicarbonate-saturated water until the pH of the water was neutral, dried with sodium sulfate, filtered and the organic solvent was removed under reduced pressure to yield 8,10-dodecadienyl acetate as a yellow liquid. This acetate was dissolved into 30 ml of methanol and 1 ml of 6 M sodium hydroxide and stirred at room temperature for two hours. Methanol was removed under reduced pressure, 10 mL of heptane and 1 mL of 1 M HCl were added and the aqueous phase removed. The organic phase was placed in a –20° C. freezer for 18 hours. White crystals were removed by filtration to yield 200 mg of E,E-8,10-dedecadienol. Gas chromatography, $^1H$ NMR and $^{13}C$ NMR analysis of the product were identical to a standard sample of E,E-8,10-dodecadienol.

EXAMPLE 4

CM pheromone is produced by a coupling reaction between 2-acetoxy-4-pentene and the same nonenyl chloride of Example 3 using the same catalyst as in Example 1, followed by hydrolysis of the coupling reaction product. The overall reaction scheme is shown below, with the details following.

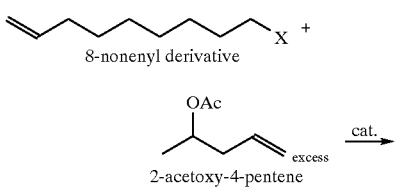

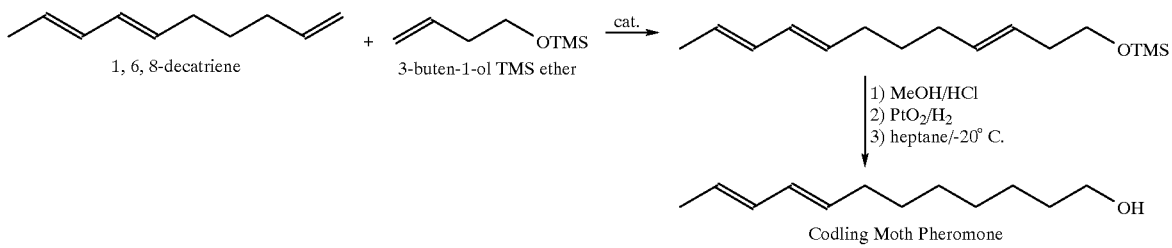

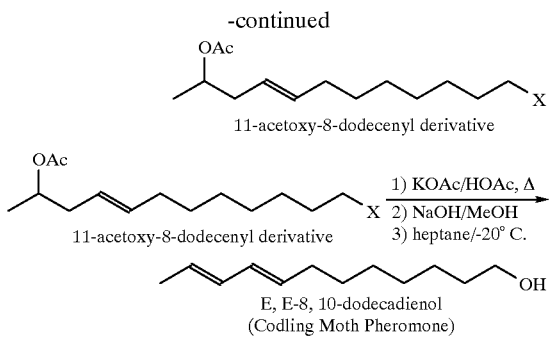

The 2-acetoxy-4-pentene starting material was produced as follows. To a 2 L round-bottomed flask containing a stir bar and a reflux condenser was added 578 g,of 1 M allyl magnesium bromide in diethyl ether. The flask was cooled to 0° C. under an atmosphere of nitrogen. Acetaldehyde (31.5 g, 715 mmol) was added over 1 hour. The reaction was stirred for additional 16 hours at room temperature. Ammonium chloride-saturated water (100 mL) and hexane (200 mL) are added. The organic phase was removed, dried with sodium sulfate, filtered and concentrated under reduced pressure. The remaining brown liquid was dissolved into 50 mL of pyridine and 60 g (594 mmol) of acetic anhydride. The reaction stirred for 12 hours. The reaction product 2-acetoxy-4-pentene was purified by washing it with 200 mL of 4 M $H_2SO_4$, 100 mL of sodium bicarbonate saturated in water and 100 mL of brine. The organic phase was dried over sodium sulfate, filtered and distilled ($Bpt_{760}$ 53°–55° C.) to yield 28 g (220 mmol, 34% yield) of 2-acetoxy-4-pentene.

The coupling reaction is performed in substantially the same manner as in Example 3. After removal of the catalyst, the reaction mixture is further heated to 125° C. with 30 mL acetic acid and 29 g (287 mmol) potassium acetate for 8 hours, then quenched by the addition of 100 mL water. The resulting organic phase is removed and stirred with 100 mL of methanol and 6 mL of 25 wt % solution of sodium hydroxide for 3 hours, then vacuum distilled and recrystallized from heptane at −20° C. to yield substantially pure CM pheromone.

EXAMPLE 5

CM pheromone is produced by a coupling reaction between 1,6,8-decatriene and 3-buten-1-ol TMS ether, followed by selective reduction of the product. The reaction scheme is summarized below, followed by details of the synthesis.

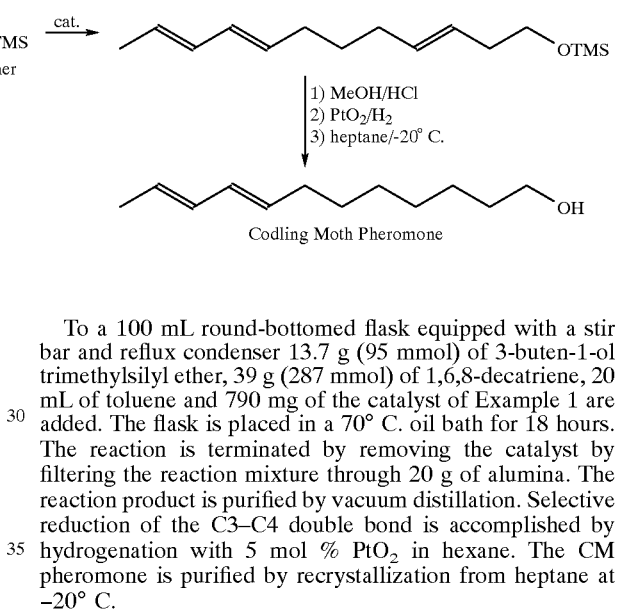

To a 100 mL round-bottomed flask equipped with a stir bar and reflux condenser 13.7 g (95 mmol) of 3-buten-1-ol trimethylsilyl ether, 39 g (287 mmol) of 1,6,8-decatriene, 20 mL of toluene and 790 mg of the catalyst of Example 1 are added. The flask is placed in a 70° C. oil bath for 18 hours. The reaction is terminated by removing the catalyst by filtering the reaction mixture through 20 g of alumina. The reaction product is purified by vacuum distillation. Selective reduction of the C3–C4 double bond is accomplished by hydrogenation with 5 mol % $PtO_2$ in hexane. The CM pheromone is purified by recrystallization from heptane at −20° C.

EXAMPLE 6

Leafroller pheromone comprises a mixture of cis- and trans-11-tetradecenyl acetate. These isomers are produced by a coupling reaction between 1-butene and 11-dodecenyl acetate using the catalyst of Example 1. The synthesis is shown below, the details of which follow.

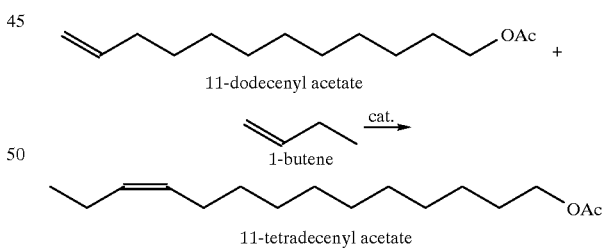

To a 100 mL round-bottomed flask containing a stir bar and dry ice condenser is added 20 g (95 mmol) of 11-dodeceyl acetate, 15.5 g (287 mmol) of 1-butene, 20 mL of toluene and 790 mg of the catalyst are added. The flask is placed in a −5° C. cooling bath for 18 hours. The reaction is terminated by removing the catalyst by filtering the reaction mixture through 20 g of alumina. The yield of the liquid 11-tetradecenyl acetate is determined by vacuum distillation.

EXAMPLE 7

Gossyplure pheromone comprises a 1:1 mixture of Z,Z and Z,E-7,11-hexadecadienyl acetates. This synthesis involves the disproportionation of 1,5-cyclooctadiene (COD) and 1-hexene to yield an approximately 1:1 mixture of Z,Z- and Z,E-1,5,9-tetradecatriene. The variance of the E isomer in the E:Z isomeric ratio of the C-11 double bond, is between 45% to 55%. 1,5,9-tetradecatriene is elongated by two carbons and acetylated to yield an approximately 1:1 mixture of Z,Z and Z,E-7,11-hexadecadienyl acetates. The Gossyplure scheme is shown below, followed by details of the synthesis.

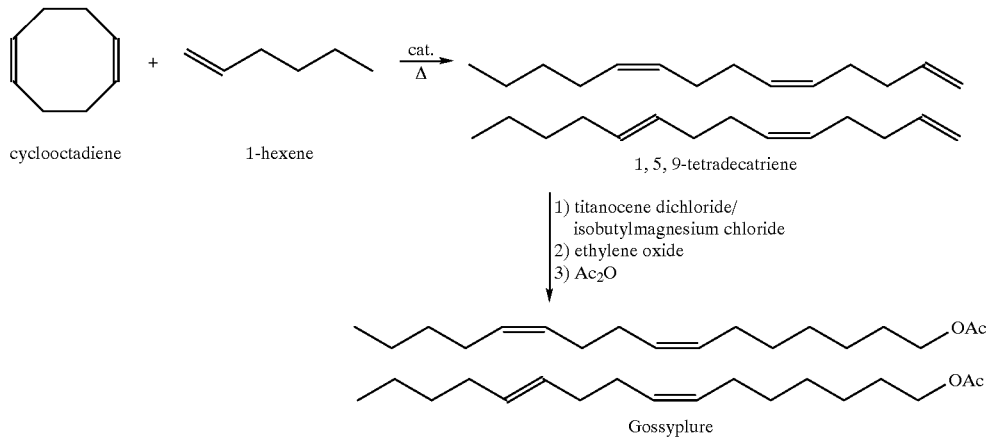

1,5,9-tetradecatriene was produced as follows. To a 125 mL Porter-Fischer tube 13 g (120 mmol) of 1,5-cyclooctadiene, 30 g (356 mmol) of 1-hexene and 0.49 g of the catalyst of Example 1 were added. The vessel was sealed and warmed to 80° C., with stirring, in an oil bath. After 3 hours, the pressure of the reaction had reached 75 psi. The reaction was cooled to room temperature and the catalyst removed by filtration through 10 g of alumina. GC analysis indicated a 30% yield of 1:1 mixture of 1,5,9-tetradecatriene (TDT).

The TDT was elongated by two carbon atoms to produce Z,Z- and Z,E-7,11-hexadecadienyl acetate as follows. To a 250 mL round-bottomed flask is added 10 g (52 mmol) of 1,5,9-tetradecatriene, 52 mL of 1.0 M isobutyl magnesium chloride in tetrahydrofuran and 0.15 g (0.6 mmol) of titanocene dichloride. This mixture was stirred at room temperature, under nitrogen, for 4 hours. The reaction is cooled to −15° C. and 3.2 mL (63 mmol) of ethylene oxide is added at a rate to maintain the temperature of the reaction between −15° and 5° C. After the ethylene oxide is added, the reaction is stirred at 0° C. for one hour. Acetic acid (20 mL) and 7.6 g (75 mmol) of acetic anhydride are added and the mixture is warmed to 45° C. for 3 hours. Excess acetic anhydride is quenched by the addition of 70 mL of an ice/water mixture. The phases are separated and the organic phase is washed with 20 mL of 1 M HCl, 10 mL of sodium bicarbonate saturated water, and 10 mL of brine. The organic phase is dried over anhydrous sodium sulfate, filtered and vacuum distilled (Bpt$_{1.0}$ 155–160° C.) to yield 7.3 g (26 mmol) of a 1:1 mixture of Z,Z and Z,E-7,11-hexadecadienyl acetates.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A method of synthesizing a biologically active compound or intermediate of the structure I H—(CH$_2$)$_z$—(CH=CH)$_a$—(CH$_2$)$_m$—(CH=CH)$_b$—(CH$_2$)$_n$—Y     I comprising reacting two dissimilar olefins, at least one of which is a terminal olefin, selected from (i) a cyclodiene containing from 7 to 12 carbon atoms and (ii) olefins of the structure II Z—HC=CH—(CH$_2$)$_r$—(—CH=CH)$_a$—(CHX)$_c$—(CH$_2$)$_t$—Y     II in the presence of a catalyst of the structure

[(PL$_3$)$_2$AA']Ru=CRR' wherein a is selected from zero, 1 and 2;

b is selected from 1 and 2;

c is selected from zero and 1;

m and n are selected from zero and an integer so that the total number of carbon atoms in the hydrocarbon chain of structure I is from 10 to 18;

r and t are integers selected so that the combined total of carbon atoms in the hydrocarbon chains of the two dissimilar olefins of structure II is from 12 to 40;

z is an integer of from 1 to 10;

X, Y and Z are independently selected from hydrogen, halide, methyl, acetyl, —CHO and —OR" wherein R" is selected from hydrogen and an alcohol protecting group selected from tetrahydropyranyl, tetrahydrofuranyl, t-butyl, trityl, ethoxyethyl and Si(R$_1$)(R$_2$)(R$_3$) wherein R$_1$, R$_2$ and R$_3$ are independently selected from alkyl and aryl;

L is selected from —CR$_4$(R$_5$)$_2$ and cycloalkyl- or alkyl-substituted cycloalkyl wherein the number of carbon atoms in the cycloalkyl ring is from 4 to 12;

R$_4$ and R5 are each selected from hydrogen and alkyl;

A and A' are anionic ligands; and

CRR' is a nonconjugated alkylidene.

2. The method of claim 1 wherein

A and A' are anionic ligands independently selected from halogen, hydrogen, C$_1$–C$_{20}$ alkyl, aryl, C$_1$–C$_{20}$ alkoxide, aryloxide, C$_2$–C$_{20}$ alkoxycarbonyl, arylcarboxylate, C$_1$–C$_{20}$ carboxylate, arylsulfonyl, C$_1$–C$_{20}$alkylsulfonyl, C$_1$–C$_{20}$ alkylsulfinyl, each ligand optionally being substituted with C$_1$–C$_5$ alkyl, halogen, $C_1$–$C_5$ alkoxy or with a phenyl group that is optionally substituted with halogen, $C_1$–$C_5$ alkyl or $C_1$–$C_5$ alkoxy; and R and R' are independently selected from hydrogen $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkysulfonyl and $C_1$–$C_{20}$ alkylsulfinyl, wherein R and R' are each optionally substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy.

3. The method of claim 1 wherein the anions A and A' are independently selected from $Cl^-$, $Br^-$, $CF_3COO^-$, $CH_3COO^-$, $CFH_2COO^-$, $CF_2HCOO^-$, $(CH_3)_3CO^-$, $(CF_3)_2CH_3CO^-$, $CF_3(CH_3)_2CO^-$, $PhO^-$, $CH_3O-$, $CH_3CH_2O^-$, $CH_3PhSO_3^-$, and $CF_3SO_3^-$.

4. The method of claim 3 wherein A and A' are independently selected from $Cl^-$, $Br^-$ and $CF_3COO^-$.

5. The method of claim 1 wherein L is selected from methyl, ethyl, propyl, butyl, pentyl, hexyl, heptyl, octyl, isopropyl, isobutyl, t-butyl, 2,2-dimethylpropyl, cyclobutyl, cyclopentyl, cyclohexyl, cycloheptyl, cyclooctyl, cyclononyl, cyclodecyl, cycloundecyl and cyclododecyl.

6. The method of claim 5 wherein L is selected from cyclopentyl and cyclohexyl.

7. The method of claim 1 wherein R and R' are independently selected from hydrogen, methyl and phenyl.

8. The method of claim 1 wherein said compound of the structure I is 1-chloro-5-decene and said two dissimilar olefins are 1-hexene and 1-chloro-5-hexene.

9. The method of claim 1 wherein said compound of the structure I is trans, trans-8,10-dodecadienol and said two dissimilar olefins are 2,4-hexadiene and $H_2C=CH-(CH_2)_7-X$ wherein X is selected from halide and $-OR_4$ wherein $R_4$ is an alcohol protecting group.

10. The method of claim 9 wherein said 2,4-hexadiene is replaced by 2-acetoxy-4-pentene.

11. The method of claim 1 wherein said compound of the structure I is 3,8,10-dodecatrienol and said two dissimilar olefins are 3-buten-1-ol trimethyl silyl ether and 1,6,8-decatriene.

12. The method of claim 1 wherein said compound of the structure I is 11-tetradecenyl acetate and said two dissimilar olefins are 1-butene and 11-dodecenyl acetate.

13. The method of claim 1 wherein said compound of the structure I is 1,5,9-tetradecatriene and said two dissimilar olefins are 1-hexene and cyclooctadiene.

* * * * *

UNITED STATES PATENT AND TRADEMARK OFFICE
CERTIFICATE OF CORRECTION

PATENT NO. : 5,916,983
DATED : June 29, 1999
INVENTOR(S) : Pederson and Grubbs

Page 1 of 1

It is certified that error appears in the above-identified patent and that said Letters Patent is hereby corrected as shown below:

Column 7,
Lines 9-12: insert the structural formula and text appearing at column 7, lines 28-31.
Lines 12-15: delete the two structural formulas, the plus (+) sign, the text and "cat.,"
Line 27: delete "-continued"
Lines 28-31: delete the structural formula and text.
Line 43: delete the comma (,) appearing after "g"
Line 47: insert -- an -- before "additional 16 hours..."

Column 8,
Lines 12-15: insert the same material deleted from column 7, lines 12-15.

Column 11,
Line 15: Change "CH$_3$O_" to read "CH$_3$O"

Signed and Sealed this

Eleventh Day of September, 2001

Attest:

NICHOLAS P. GODICI
*Attesting Officer*   *Acting Director of the United States Patent and Trademark Office*